United States Patent [19]

Mayfield et al.

[11] Patent Number: 5,082,652
[45] Date of Patent: Jan. 21, 1992

[54] AEROSOL DEODORANT COMPOSITION AND PACKAGED AEROSOL DEODORANT

[76] Inventors: Larry Mayfield, 12 Corwin St., Kenvil, N.J. 07847; Thomas Russo, 28 Shore Rd., Andover, N.J. 07821; Kenneth Klausner, 28 S. Brookside Dr., Rockaway, N.J. 07866; Charles Shalotsky, 14 Van Doren Ave., Chatham, N.J. 07928

[21] Appl. No.: 408,906

[22] Filed: Aug. 22, 1989

[51] Int. Cl.$^5$ ................................................ A61K 7/32
[52] U.S. Cl. ...................................... 424/47; 424/65; 424/66; 424/67; 424/68
[58] Field of Search ........................ 424/43, 47, 65, 66, 424/67, 68; 222/394

[56] References Cited

U.S. PATENT DOCUMENTS 3,207,386 9/1965 Presant et al. ........................ 424/47
4,861,584 8/1989 Powell, Jr. et al. .................. 424/45
4,863,721 9/1989 Beck et al. ............................ 424/47

Primary Examiner—Thurman Page

[57] ABSTRACT

Disclosed is an aerosol deodorant composition which includes an aerosol propellant, a volatile low-viscosity fluid, an oil absorbent particulate material, a silicone polymer and a deodorancy agent, such as at least one of a fragrance and a bactericide. The addition of the oil absorbent particulate material prevents dusting of liquid particles, and the addition of the silicone polymer prevents dusting by the oil absorbent particulate material. Also disclosed is an aerosol deodorant package including the aerosol deodorant composition and an aerosol delivery system having a valve which has orifices for passing the aerosol deodorant composition out of the package, the orifices having diameters such that the average delivery rate of the aerosol deodorant composition from the package is at most 0.44 gm/sec.

29 Claims, 2 Drawing Sheets

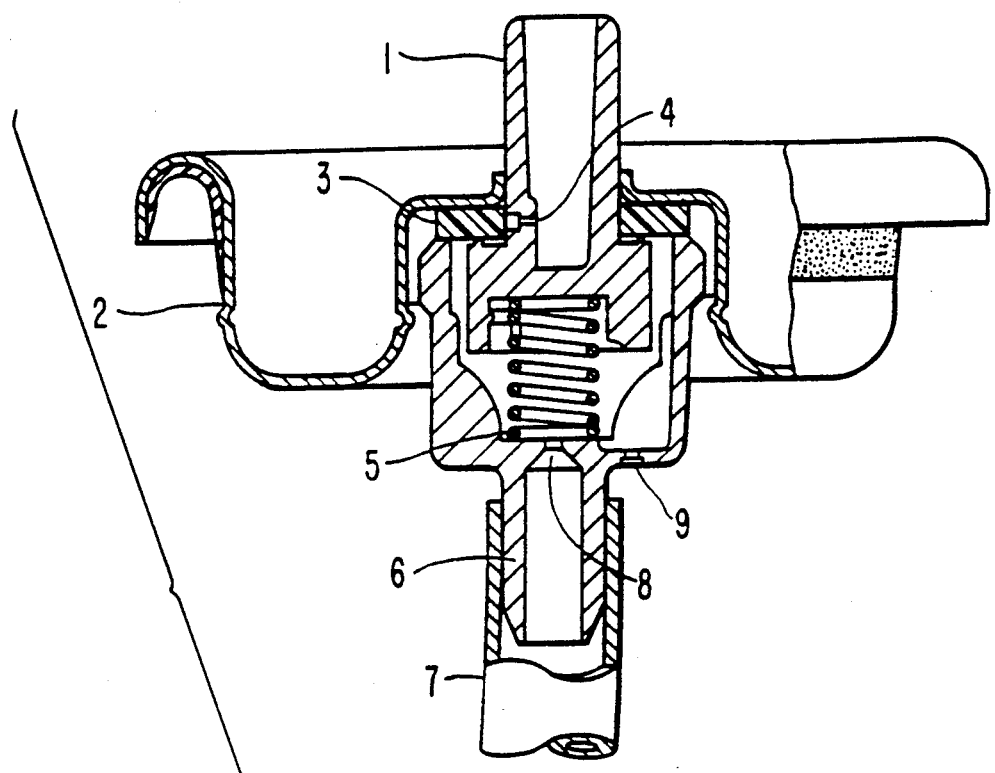
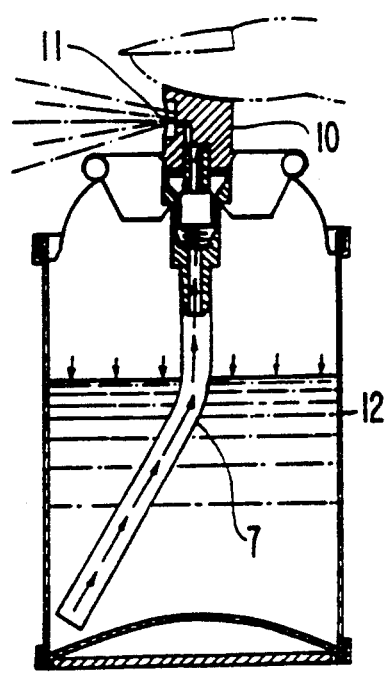

AEROSOL DEODORANT COMPOSITION AND PACKAGED AEROSOL DEODORANT

To be noted is pending United States patent application Ser. No. 07/199,267 filed May 26, 1988, entitled "Aerosol Antiperspirant Composition, Including Substantivity Fluid, Capable of Being Dispensed At Reduced Spray Rate, and Packaged Aerosol Antiperspirant", now U.S. Pat. No. 4,935,224 issued June 19, 1990 which is incorporated herein by reference in its entirety.

BACKGROUND OF THE INVENTION

The present invention relates to an aerosol deodorant composition, delivered to the skin (e.g., the axillae) of a person through use of an aerosol delivery system, and to such composition packaged with the aerosol delivery system. By such an aerosol delivery system, deodorant composition is directed to the skin in the form of a finely divided spray.

Fresh perspiration is nearly odorless in healthy people. It is the breakdown of the perspiration by a variety of skin bacteria that creates the decomposition products that are responsible for typical body malodors. To prevent the formation of unpleasant body odors, there are three approaches: (1) suppression of perspiration, (2) stop and/or reduce the development of skin bacteria, and (3) masking or sorption of the odor.

A deodorant is an agent which removes, corrects or prevents undesirable odors. Deodorants prevent, neutralize or mask the objectionable odors resulting from the degradation of the components of perspiration due to chemical and microbial attack into, e.g., foul-smelling fatty acids. Antiperspirants, on the other hand, combat axillary odors by inhibiting perspiration through the action of astringent salts such as aluminum and zirconium salts. While an antiperspirant may be considered to be a type of deodorant since it prevents odor by eliminating perspiration, the term "deodorant" as used in the subject application is not intended to encompass agents such as antiperspirants which inhibit perspiration by use of astringent salts (that is, the present invention does not encompass antiperspirant compositions including astringent salts). Thus, the present invention is concerned with compositions that have only a deodorant effect, that is, they do not check the flow of perspiration to any appreciable extent.

With aerosol deodorants, a major problem is the dust or mist cloud which arises when the product is sprayed and applied to the skin. This dust or mist cloud causes a major consumer complaint; that is, choking and coughing caused by such dust or mist cloud.

There are two factors which contribute to the development of this dust or mist cloud. The first is the fine dusting initially produced at the site of the actuator button orifice of conventional valves utilized to deliver the finely divided spray. In dispersion-type aerosol deodorants delivered by conventional aerosol packaging devices, fine particles are quickly scattered into the air with the expanding propellant(s).

A second factor for the development of the dust or mist cloud is product bounce-off. In conventional aerosol deodorant compositions, there is low product adhesion during spraying to the underarm area, which results in over-spray and more product bouncing off and becoming air-borne.

Moreover, conventional aerosol deodorant compositions have relatively large valve orifices for the aerosol delivery system and have resulting relatively large spray rates, giving rise to an objectionable "cold" feeling upon application of the product to the skin and also increasing bounce-off of the product. Such relatively large orifice sizes are necessary to avoid clogging of the orifices by the spray.

In addition, conventional aerosol deodorant compositions usually contain alcohol in amounts which contribute to mist formation and which can be irritating to the skin.

U.S. Pat. No. 4,152,416 to Spitzer et al discloses that, with conventional aerosol delivery systems of the vapor tap-type, having a button orifice diameter of 0.016 inch, a stem orifice of 0.018 inch in diameter, a vapor tap orifice of 0.023 inch in diameter and a capillary dip tube 0.050 inch in diameter, clogging of the orifices is caused in dispensing an aluminum antiperspirant composition containing dispersed astringent salt particles. Moreover, the vapor tap-type of valve requires a high proportion of propellant in the aerosol composition, giving rise to a product that is delivered with a large amount of mistiness and dustiness (that is, the aerosol composition that is dispersed gives rise t stable aerosols of finely divided liquid particles and produces a fine dust). This patent goes on to disclose aerosol antiperspirant compositions capable of dispensing active astringent salt, in particulate form, from aerosol containers with low mistiness and dustiness. The astringent salt (such as aluminum chlorhydroxide or other antiperspirant aluminum and/or zirconium salts), in particulate form, is utilized in the antiperspirant composition at relatively high concentrations, yet can be delivered with low mistiness and low dustiness. This patent discloses that the described aerosol antiperspirant compositions include, in combination, an astringent salt in an amount within a range from about 3% to about 30%; a liquid phase comprising a propellant in an amount within a range from about 15% to about 95%; a synthetic polymer gum having a viscosity within a range from about 500,000 to about 100 million centistokes at 25° C., in an amount within a range from about 0.05% to about 5% by weight of the composition, to increase the viscosity of the liquid phase and inhibit mistiness and dustiness; and, optionally, a non-volatile miscible organic liquid in an amount within a range from about 0.1% to about 30% by weight of the composition, of which organic liquid all or part optionally comprises an aliphatic, cycloaliphatic or aromatic carboxylic acid having from about 9 to about 50 carbon atoms that enhances adhesion of the antiperspirant salt to the skin.

The aforementioned U.S. patent further discloses that the polymer gums are either soft or rubbery solids, or highly viscous materials, being soluble in the liquid phase (including the propellant and any non-volatile liquid); and that silicone gums and especially silicone polymers of the dimethylpolysiloxane type, and acrylic and hydrochloric polymers, are preferred. This patent further discloses that it is important that the polymer gum be soluble in the liquid phase of the composition, and that it is advantageous but not essential that the polymer be soluble in the non-volatile oil component of the composition. The patent additionally specifies that if the polymer is not soluble and is of a rubbery or soft solid consistency, residues in the valve or actuator button may have a tendency to cause clogging, which can be avoided by adding a lubricant. This patent additionally discloses that silicone oils are useful lubricants to avoid clogging and so also may be the non-volatile organic liquid. In the specific examples in this patent, the valve or actuator button orifice and the stem orifice are larger than those of the previously discussed conventional vapor tap-type aerosol delivery system. U.S. Pat. No. 4,152,416 to Spitzer et al. is incorporated herein in its entirety by reference.

While disclosing an aerosol antiperspirant composition which avoids some of the grounds of consumer dissatisfaction with aerosol antiperspirants containing astringent salt particulates, U.S. Pat. No. 4,152,416 is not directed to aerosol deodorant compositions which do not contain astringent salt particulates.

Moreover, additional improvements are desired, especially with respect to aerosol deodorant compositions. Such deodorant compositions suffer from dustiness problems due to increased dusting by liquid particles.

Thus, there exists a need for improved aerosol deodorant compositions and aerosol delivery systems for delivering such compositions, avoiding various problems still arising in connection with aerosol deodorant compositions. Specifically, there is still a need to provide aerosol deodorant compositions wherein dusting, bouncing-off of the sprayed product and an objectionable "cold" feel of the sprayed product are avoided, and clogging of valves of the aerosol delivery system is also avoided. There is also a need to provide an aerosol deodorant composition having improved product adhesion and less irritation. There is also a need to provide an aerosol deodorant composition which can be delivered at a low delivery (spray) rate, while avoiding clogging of the valve. There is also a need for apparatus (for example, an aerosol delivery system) and techniques, used in connection with the composition, so as to avoid the above-mentioned bounce-off problems and objectionable "cold" feel of the sprayed product.

While various of U.S. Pat. Nos. 4,053,581 to Pader et al.; 4,065,564 to Miles et al.; 4,073,880 to Pader et al.; and 4,423,041 to Clum et al., as well as European Patent Application No. 197,485, disclose compositions, including antiperspirant compositions, containing silicone materials, none of these documents discloses aerosol deodorant compositions having improved product adherence to the skin, with greater resistance to washing-off and rubbing-off. Moreover, none of these references discloses compositions which can be delivered at reduced spray (delivery) rates, without clogging of the aerosol valve. None of the references even discloses the desirability of decreasing the delivery rate so as to avoid the objectionable "cold" feeling upon delivery and to decrease product bounce-off, dustiness and mistiness.

SUMMARY OF THE INVENTION

The present invention solves the above-noted problems encountered in the prior art and provides an aerosol deodorant composition including an aerosol propellant, a volatile low-viscosity fluid, an oil absorbent particulate material, a silicone polymer, and a deodorant active material. Preferably, the aerosol deodorant composition includes at least one material selected from the group consisting of fragrance and bactericide as the deodorant active material. The term "deodorant active material" as used herein means a material, other than an astringent salt, which obviates odor. A deodorant active material reduces perspiration odor either by stopping or reducing the development of skin bacteria or by masking and/or adsorption of the malodors caused by bacterial degradation of perspiration. The deodorant composition of the present invention consists essentially of the foregoing components and, e.g., does not contain an antiperspirant active material such as an astringent salt.

The volatile low-viscosity fluid is preferably a volatile low-viscosity hydrocarbon fluid, more preferably a low-viscosity silicone fluid and, most preferably, cyclomethicone, hexamethyldisiloxane and/or dimethicone.

The oil absorbent particulate material is preferably at least one material selected from the group consisting of talc, starch, clay, microcrystalline cellulose and cereal grain flour, and is preferably homogeneously dispersed in the volatile low-viscosity fluid.

The silicone polymer is preferably a silicone gum, more preferably polydimethylsiloxane gum and, most preferably, dimethiconol.

The aerosol deodorant composition may also contain a clay suspending or thickening agent which can be, for example, in the form of a gel in a non-polar vehicle. The clay may be at least one of bentonite, hectorite, colloidal magnesium aluminum silicate or hydrophobically treated bentonite prepared by reacting bentonite in a cation exchange system with an amine.

The aerosol deodorant composition ma be nonalcoholic or may contain 1.0% or less alcohol by weight. The aerosol deodorant composition is also preferably anhydrous.

The aerosol deodorant composition may also contain antioxidants, such as BHA, BHT, tocopherol and its salts, ascorbic acid and its salts, etc.

The present invention also provides an aerosol deodorant package including the aforementioned aerosol deodorant composition and an aerosol delivery system having a valve, and a method of applying a deodorant using such package, the valve having orifices for passing the aerosol deodorant composition out of the package, the orifices having diameters such that the average delivery rate (the arithmetic mean delivery rate through the life of the unit) of the aerosol deodorant composition from the package is at most 0.44 gm/sec.

Desirably, the combination of silicone polymer dispersed in the volatile low-viscosity fluid forms a skin substantivity fluid which reduces dusting originating at the spray orifice and also avoids product bounce-off. Moreover, the substantivity fluid gives the product increased resistance to being washed-off or rubbed-off, i.e., the product has greater adhesion to the skin. The silicone polymer and at least a portion of the volatile low-viscosity fluid can be introduced into the composition as a substantivity fluid. Various compositions are commercially available which may be used as a substantivity fluid in the aerosol deodorant composition of the present invention.

BRIEF DESCRIPTION OF THE DRAWINGS

FIG. 1 is a view of a vapor tap-type valve assembly, without the actuator assembly, which may be used as part of the present invention;

FIG. 2 is a view of an aerosol container of the present invention using the vapor tap-type valve of FIG. 1.

DETAILED DESCRIPTION OF THE INVENTION

Figure 3:
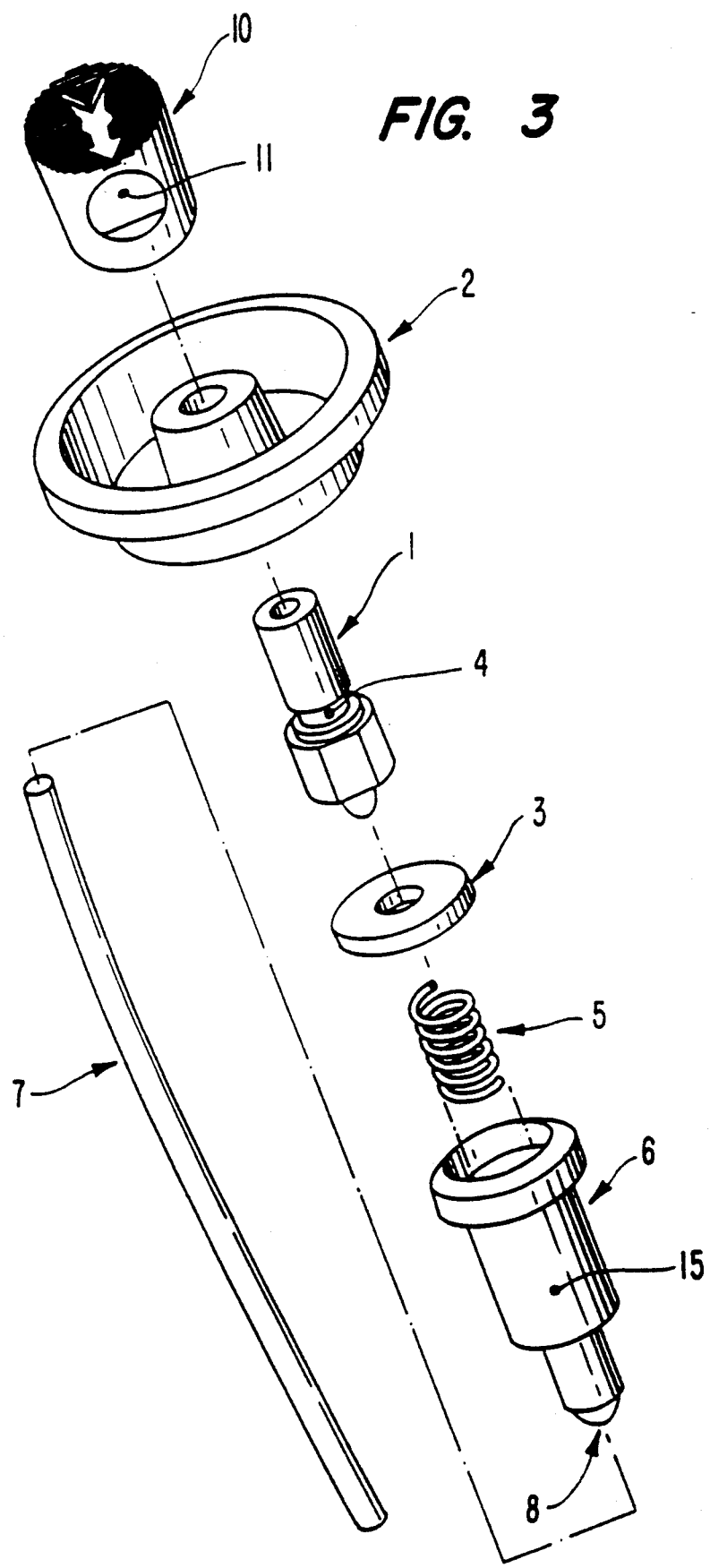
FIG. 3 is an exploded view of a second type of vapor tap-type valve which may be used as part of the present invention.

The aerosol deodorant composition of the present invention includes an aerosol propellant, a volatile low-viscosity fluid, an oil absorbent particulate material, a silicone polymer, and a deodorant active material. The deodorant active material is preferably at least one material selected from the group consisting of fragrance and bactericide.

As previously mentioned, conventional aerosol deodorant compositions do not contain solid particulate material such as astringent salt particles. Accordingly, such deodorant compositions suffer from greater dustiness problems due to dusting by liquid particles. In order to solve this problem, the aerosol deodorant composition of the present invention includes an oil absorbent particulate material. The oil absorbent particulate material is an aerosol grade particulate material which preferably has particles with diameters under 50 microns. The oil absorbent particulate material is preferably talc. Most preferably, substantially all particles (e.g., 98%) have diameters less than 15 microns. For example, the talc can have the following typical particle size distribution:

| Microns | % Less Than |
|---|---|
| 15 | 98 |
| 10 | 98 |
| 5 | 90 |
| 3 | 75 |
| 2 | 60 |
| 1 | 50. |

However, other oil absorbent particulate materials may also be incorporated alone or in various combinations with or without talc. Other oil absorbent particulate materials include, e.g., starches, clays, micro-crystalline cellulose and cereal grain flour. The oil absorbent particulate material is preferably homogeneously dispersed in the volatile low-viscosity fluid.

In order to prevent dusting of the oil absorbent particulate material, the aerosol deodorant composition of the present invention also includes a silicone polymer.

As the silicone polymer used in the present invention, silicone gum is particularly noted. These gums are defined in U.S. Pat. No. 4,152,416, the contents of which have already bee incorporated herein by reference. Briefly, this patent discloses incorporating silicone gums having a viscosity within the range from about 500,000 to 100 million centistokes at 25° C. as part of the aerosol antiperspirant composition. Such silicone gums (for example, polydimethylsiloxane polymers) as disclosed in U.S. Pat. No. 4,152,416 are also applicable in the aerosol deodorant composition of the present invention. An example of a specific silicone gum is dimethiconol having the aforementioned viscosity.

As for the volatile low-viscosity fluid component incorporated into the aerosol deodorant composition, various volatile silicone liquids can be utilized. One series of such volatile liquids, which are preferred volatile liquids for the present invention, are the cyclomethicone and dimethicone liquids. However, the present invention is not limited to the use of cyclomethicone or dimethicone liquids as the volatile low-viscosity fluid incorporated in the aerosol deodorant compositions. Specifically, volatile linear silicone liquids, as well as volatile hydrocarbon liquids, in which the silicone polymer (e.g., silicone gum) is soluble, can be utilized for the present invention. Generally, the volatile low-viscosity liquids usable for the present invention have a boiling point of at least 212° F. (for example, 212° F.–500° F.). Moreover, the volatile low-viscosity liquid should have a viscosity of less than 10 centistokes at 25° C.

Various volatile low-viscosity fluids which may be used in the present invention ar set forth in the following Table 1.

TABLE 1

| Volatile Fluid | Flash Point (°F.) | Viscosity (Centistokes at 25° C.) |
|---|---|---|
| SWS* F-221 Hexamethyldisiloxane | 30 | 0.65 |
| SWS F-222 Decamethylcyclopentasiloxane | 157 | 4.0 |
| SWS 03314 Octamethylcyclotetrasiloxane | 126 | 2.3 |
| SWS 251 Cyclic Dimethylsiloxane | 150 | 3.1 |
| Dow Corning 245 | 170 | 4.2 |
| Dow Corning 345 | 165 | 5.0 |
| Dow Corning 244 | 131 | 2.5 |
| Dow Corning 344 | 125 | 2.5 |
| Dow Corning 200 Hexamethyldisiloxane | 30 | 0.65 |
| Union Carbide VS-7158 | 170 | 4.0 |
| Union Carbide VS-7207 | 130 | 2.3 |
| Union Carbide VS-7349 | 132 | 2.5 |
| General Electric SF-1173 | 130 | 2.4 |
| General Electric SF-1202 | 170 | 4.1 |
| General Electric SF-1204 | 130 | 2.5 |

*SWS Silicones Corporation (Adrian, Michigan)

As can be seen from the foregoing Table 1, flash points of these illustrative volatile fluids range from 30° F. to 170° F.

As previously indicated, while various cyclomethicone compounds have been specifically disclosed above as the volatile low-viscosity component incorporated a part of the aerosol deodorant compositions of the present invention, the present invention is not limited thereto; and, specifically, low molecular weight straight-chain silicone fluids such as hexamethyldisiloxane and dimethicone, as well as volatile hydrocarbon fluids, may be utilized within the scope of the present invention. As the hydrocarbon fluid, various Permethyl hydrocarbons (aliphatic hydrocarbons), products of Permethyl Corporation (Frazer, Pennsylvania) may be utilized. Such hydrocarbons include Permethyl 99A, 101A, 102A and 104A.

As indicated above, the silicone polymer and at least a portion of the volatile low-viscosity fluid can be introduced in the composition as a skin substantivity fluid which reduces dusting originating at the spray orifice, and also avoids product bounce-off. Moreover, by incorporating such a substantivity fluid, the applied product has increased resistance to being washed off or rubbed off and has greater adhesion to the skin. Representative substantivity fluids contain a polydimethylsiloxane polymer (e.g., viscosity over 30 million centistokes at 25° C.) and a cyclomethicone to form a low viscosity fluid (between 3,000 to 7,000 centistokes at 25° C.). A specific substantivity fluid usable within the scope of the present invention is Dow Corning Q2-1401 fluid, containing 85–88% by weight cyclomethicone and 12–15% by weight silicone polymer (dimethiconol). Thus, this substantivity fluid contains 100% silicone materials, with 12–15% non-volatile content. This is a preferred substantivity fluid to be used in the present invention. Illustratively, this Dow Corning Q2-1401 fluid can be incorporated in the aerosol deodorant composition so as to provide silicone gum levels in the composition of at least 0.05%, preferably 0.05 - 1.5%, by weight of the total weight of the aerosol deodorant composition. At levels of dimethiconol (silicone gum) in the cyclomethicone in Q2-1401 (that is, 12-15% dimethiconol), the dimethiconol is completely soluble in the cyclomethicone. Generally, dimethiconol can be completely dissolved in cyclomethicone at levels up to 50% by weight.

Another substantivity fluid which may be used in the present invention is General Electric SF-1214. This fluid is a blend of 85% by weight cyclomethicone and 15% by weight silicone gum (dimethicone). This fluid has a viscosity of 4,000 to 8,000 centistokes at 25° C.

Accordingly, by the present invention, including incorporation of the oil absorbent particulate material and the silicone polymer (forming, in combination with at least a portion of the volatile low-viscosity fluid, a substantivity fluid) in the aerosol deodorant composition, dustiness of aerosol deodorant compositions upon application to the underarm can be avoided, while delivering the deodorant composition at a relatively low delivery rate, avoiding clogging of the valve of the aerosol delivery system and increasing deposition of the deodorant composition.

As previously mentioned, the aerosol deodorant composition of the present invention includes at least an aerosol propellant. Various propellants which may be used are disclosed in U.S. Pat. No. 4,152,416, the contents of which have previously been incorporated herein by reference, and include chemically inert hydrocarbons such as propane, n-butane, isobutane and cyclopropane, as well as halogenated hydrocarbons such as dichlorodifluoromethane (Propellant 12) and 1,1-dichloro-1,1,2,2-tetrafluoroethane (Propellant 114), among other known propellants. Additional propellants include A-31 propellant (isobutane) and A-46 propellant (a mixture of isobutane and propane and butane).

The aerosol deodorant composition of the present invention also includes at least one material selected from the group consisting of fragrance and bactericide. The fragrance ca deodorize by masking objectionable odors. Various fragrances well known in the art may be included, such as decyl alcohol, citral, eugenol, cinnamic aldehyde, phenylethyl alcohol, thyme oil, oil of cloves, spikenard oil, etc. The bactericide deodorizes by killing bacteria present on the skin which cause objectionable odors. Various bactericides known in the art, such as Triclosan, benzethonium chloride, steapyrium chloride, PPG-9 diethylmonium chloride, PPG-25 diethylmonium chloride, phenoxyethanol, etc., may be employed.

Other deodorancy agents, including compounds which deprive odor-causing bacteria of critical metal nutrients required by the bacteria for enzymic formation of free acids, and/or compounds which restrict adherence of odor-causing bacteria to the axillary region, known in the art, can be incorporated in the aerosol deodorant compositions of the present invention.

The aerosol deodorant composition of the present invention may include additional ingredients such as esters, e.g., isopropyl palmitate. Such esters serve as a carrier for, e.g., a fragrance.

The aerosol deodorant composition may also contain antioxidants, such as BHA, BHT, tocopherol and its salts, ascorbic acid and its salts, etc.

In order to prevent caking or settling out of the various ingredients, a suspending or thickening agent may be incorporated. A clay suspending or thickening agent in the form of a gel in a non-polar vehicle is preferred. The clay may comprise bentonite, hectorite, colloidal magnesium aluminum silicate or hydrophobically treated bentonite prepared by reacting bentonite in a cation exchange system with an amine.

The foregoing ingredients can be incorporated in the aerosol deodorant composition in the following weight percentage ranges:

Propellant: 3014 90%, preferably 60-85%
Volatile low-viscosity fluid: 1-40%, preferably 10-20%
Oil absorbent particulate material: 0.3-15%, preferably 0.5-10%
Silicone polymer: 0.05-3%, preferably 0.10-2.0%
Fragrance: 0-3%, preferably 0.10-2.0%
Bactericide: 0-1.0%, preferably 0-0.5%
Esters: 0-10%, preferably 1.0-3.0%
Thickening agent: 0-5%, preferably 1.0-4.0%.

The composition is preferably non-alcoholic or contains 1% or less, preferably 0.5% or less, alcohol. The composition is preferably anhydrous.

The present aerosol deodorant composition can be delivered utilizing aerosol containers with aerosol valves of the vapor tap-type, but having smaller orifice openings (and a resulting decreased delivery rate) than those described in U.S. Pat. No. 4,152,416. Generally, known aerosol valves having relatively small orifice sizes can be used in the present invention. As illustrative of aerosol containers capable of delivering fine-divided sprays, and not limiting, see U.S. Pat. Nos. 3,083,917 and 3,083,918 to Abplanalp et al., and U.S. Pat. No. 3,544,258 to Presant et al. The contents of each of U.S. Pat. Nos. 3,083,917, 3,083,918 and 3,544,258 are incorporated herein by reference.

FIG. 1 shows a valve assembly usable in the present invention. Stem 1 extends through mounting cup 2 which forms the top of the aerosol container; gasket member 3 acts to close the stem orifice 4 in the absence of downward pressure so as to close the valve. Spring 5 forces stem 1 against the gasket member 3 so as to close off the stem orifice 4. The other end of the spring 5 pushes against body 6; in passing from the aerosol container, the composition passes through dip tube 7 into body 6, the composition passing through the body orifice 8 in the body 6. The composition then passes into stem 1 through stem orifice 4, into actuator button 10 (shown in FIG. 2) and out of the package through button orifice 11 (see FIG. 2). Also shown in FIG. 1 is vapor tap 9.

FIG. 3 shows a different valve assembly, in an exploded view. In FIG. 3, the same reference characters as in FIGS. 1 and 2 have been used to represent the same structure. Note that FIG. 3 shows button orifice 11 and shows vapor tap 15 in the side of body 6. Also shown in FIG. 2 is container 12.

It is preferred to have a relatively small button orifice diameter (e.g., 0.013 inch–0.020 inch) in order for the spray to be wide (which is the preferred spray pattern). The diameter of the stem orifice should also be relatively small so as to provide a wide spray pattern.

It is desirable for purposes of application of a spray of the aerosol deodorant composition of the present invention that the diameters of the stem and vapor tap orifices be relatively small; these are the orifices which are most important in determining spray rate. Thus, for purposes of the present invention, the stem orifice and vapor tap should be of such a diameter that the spray (delivery) rate of the aerosol deodorant composition is at most 0.5 gm/sec.

A specific example of a preferred valve assembly will now be set forth. Of course, such specific example is illustrative and not limiting; variations depending, for example, on the specific design of the valve assembly (dependent on the manufacturer) would be within the skill of the art. Thus, using a Seaquist valve, the following orifice diameters can be used:

- Stem orifice: 0.013 inch
- Body orifice: 0.018 inch
- Vapor tap: 0.013 inch
- Button (actuator): an orifice of 0.016 inch; the button had an insert providing further mechanical break-up of the spray.

The container can be loaded with the aerosol deodorant composition at a pressure of 25–55 PSIG. For example, using the above-described valve assembly with an aerosol container loaded with an aerosol deodorant composition at a pressure of 35 PSIG at 70° F., the initial delivery rate can be about 0.32 gm/sec, while at a pressure of 50 PSIG at 70° F., the initial delivery rate can be about 0.44 gm/sec.

By the present invention, including the relatively low delivery rate and the aerosol deodorant composition, the delivery rate can be kept relatively constant at the relatively low rate until about 90–95% of the contents of the container have been expelled, without clogging of the orifices.

Following are specific examples of the present invention utilizing Dow Corning Q2-1401 and other substantivity fluids. Of course, as may be seen from the foregoing, the invention is not limited to the use of such substantivity fluids. To the contrary, it is intended to cover all alterations, modifications and equivalents as may be included within the spirit and scope of the invention as defined by the appended claims.

In the following examples, all percentages of the specified ingredients are weight percentages. Moreover, the Dow Corning Q2-1401 fluid contained 87% by weight cyclomethicone and 13% by weight dimethiconol (a polydimethylsiloxane polymer). Where applicable, the designation of the ingredients is the CFTA designation. The fragrance selected should be one that has been screened as being an effective masking agent, e.g., Noville #31138. The A-31 propellant is isobutane, while the A-46 propellant is a mixture of isobutane, propane and butane.

EXAMPLE 1

An aerosol deodorant composition was prepared having the following formulation:

| Ingredients | % by Weight |
|---|---|
| Cyclomethicone | 20.370 |
| Isopropyl palmitate | 2.905 |
| Q2-1401 fluid (87% by weight cyclomethicone, 13% by weight dimethiconol) | 5.600 |
| Bactericide (Triclosan) | 0.070 |
| Fragrance | 1.505 |
| Talc | 1.750 |
| Bentone gel | 2.800 |
| Subtotal Concentrate (without propellant) | 35.000 |
| A-31 propellant | 65.000 |
| | 100.000 |

EXAMPLE 2

An aerosol deodorant composition was prepared having the following formulation:

| Ingredients | % by Weight |
|---|---|
| Cyclomethicone | 20.370 |
| Isopropyl palmitate | 2.905 |
| Q2-1401 fluid (87% by weight cyclomethicone, 13% by weight dimethiconol) | 5.600 |
| Bactericide (Triclosan) | 0.070 |
| Fragrance | 1.505 |
| Talc | 1.750 |
| Bentone gel | 2.800 |
| Subtotal Concentrate (without propellant) | 35.000 |
| A-46 propellant | 65.000 |
| | 100.000 |

EXAMPLE 3

An aerosol deodorant composition was prepared having the following formulation:

| Ingredients | % by Weight |
|---|---|
| Cyclomethicone | 10.800 |
| Isopropyl palmitate | 2.075 |
| Q2-1401 fluid (87% by weight cyclomethicone, 13% by weight dimethiconol) | 4.000 |
| Bactericide (Triclosan) | 0.050 |
| Fragrance | 1.075 |
| Talc | 5.000 |
| Bentone gel | 2.000 |
| Subtotal Concentrate (without propellant) | 25.000 |
| A-31 propellant | 75.000 |
| | 100.000 |

EXAMPLE 4

An aerosol deodorant composition was prepared having the following formulation:

| Ingredients | % by Weight |
|---|---|
| Cyclomethicone | 10.800 |
| Isopropyl palmitate | 2.075 |
| Q2-1401 fluid (87% by weight cyclomethicone, 13% by weight dimethiconol) | 4.000 |
| Bactericide (Triclosan) | 0.050 |
| Fragrance | 1.075 |
| Talc | 5.000 |
| Bentone gel | 2.000 |
| Subtotal Concentrate (without propellant) | 25.000 |
| A-46 propellant | 75.000 |
| | 100.000 |

EXAMPLE 5

An aerosol deodorant composition was prepared having the following formulation:

| Ingredients | % by Weight |
| --- | --- |
| Cyclomethicone | 14.125 |
| Isopropyl palmitate | 2.075 |
| Q2-1401 fluid (87% by weight cyclomethicone, 13% by weight dimethiconol) | 4.000 |
| Bactericide (Triclosan) | 0.050 |
| Fragrance | 1.500 |
| Talc | 1.250 |
| Bentone gel | 2.000 |
| Subtotal Concentrate (without propellant) | 25.000 |
| A-46 propellant | 75.000 |
| | 100.000 |

EXAMPLE 6

An aerosol deodorant composition was prepared having the following formulation:

| Ingredients | % by Weight |
| --- | --- |
| Cyclomethicone | 10.375 |
| Isopropyl palmitate | 2.075 |
| Q2-1401 fluid (87% by weight cyclomethicone, 13% by weight dimethiconol) | 4.000 |
| Bactericide (Triclosan) | 0.050 |
| Fragrance | 1.500 |
| Talc | 5.000 |
| Bentone gel | 2.000 |
| Subtotal Concentrate (without propellant) | 25.000 |
| A-46 propellant | 75.000 |
| | 100.000 |

EXAMPLE 7

An aerosol deodorant composition was prepared having the following formulation:

| Ingredients | % by Weight |
| --- | --- |
| Cyclomethicone | 12.275 |
| Isopropyl palmitate | 2.075 |
| Q2-1401 fluid (87% by weight cyclomethicone, 13% by weight dimethiconol) | 4.000 |
| Bactericide (Triclosan) | 0.050 |
| Fragrance | 1.500 |
| Talc | 3.100 |
| Bentone gel | 2.000 |
| Subtotal Concentrate (without propellant) | 25.000 |
| A-46 propellant | 75.000 |
| | 100.000 |

EXAMPLE 8

An aerosol deodorant composition was prepared having the following formulation:

| Ingredients | % by Weight |
| --- | --- |
| Cyclomethicone | 12.275 |
| Isopropyl palmitate | 2.075 |
| Q2-1401 fluid (87% by weight cyclomethicone, 13% by weight dimethiconol) | 4.000 |
| Bactericide (Triclosan) | 0.050 |
| Fragrance | 1.500 |
| Talc | 3.100 |
| Bentone gel | 2.000 |
| Subtotal Concentrate (without propellant) | 25.000 |
| A-31 propellant | 75.000 |
| | 100.000 |

EXAMPLE 9

An aerosol deodorant composition was prepared having the following formulation:

| Ingredients | % by Weight |
| --- | --- |
| Hexamethyldisiloxane | 6.925 |
| Isopropyl palmitate | 6.925 |
| Q2-1401 fluid (87% by weight cyclomethicone, 13% by weight dimethiconol) | 4.000 |
| Bactericide (Triclosan) | 0.050 |
| Finsolv TN | 3.250 |
| Fragrance | 0.600 |
| Talc | 1.250 |
| Bentone gel | 2.000 |
| Subtotal concentrate (without propellant) | 25.000 |
| A-31 propellant | 75.000 |
| | 100.000 |

Finsolv TN (CFTA name: $C_{12-15}$ Alcohols Benzoate) is available form Finetex, Inc., Southern Division of Spencer, North Carolina, and is a non-oily ester used to solubilize the fragrance and impart a dry talc-like feel. It may be considered a partial replacement for isopropyl palmitate.

EXAMPLE 10

An aerosol deodorant composition was prepared having the following formulation:

| Ingredients | % by Weight |
| --- | --- |
| Hexamethyldisiloxane | 9.695 |
| Isopropyl palmitate | 9.695 |
| Q2-1401 fluid (87% by weight cyclomethicone, 13% by weight dimethiconol) | 5.600 |
| Bactericide (Triclosan) | 0.070 |
| Finsolv TN | 4.550 |
| Fragrance | 0.840 |
| Talc | 1.750 |
| Bentone gel | 2.800 |
| Subtotal concentrate (without propellant) | 35.000 |
| A-31 propellant | 65.000 |
| | 100.000 |

EXAMPLE 11

An aerosol deodorant composition was prepared having the following formulation:

| Ingredients | % by Weight |
| --- | --- |
| Hexamethyldisiloxane | 8.310 |
| Isopropyl palmitate | 8.310 |
| Q2-1401 fluid (87% by weight cyclomethicone, 13% by weight dimethiconol) | 4.800 |
| Bactericide (Triclosan) | 0.060 |
| Finsolv TN | 3.900 |

-continued

| Ingredients | % by Weight |
|---|---|
| Fragrance | 0.720 |
| Talc | 1.500 |
| Bentone gel | 2.400 |
| Subtotal concentrate (without propellant) | 30.000 |
| A-31 propellant | 70.000 |
| | 100.000 |

EXAMPLE 12

An aerosol deodorant composition was prepared having the following formulation:

| Ingredients | % by Weight |
|---|---|
| Hexamethyldisiloxane | 21.140 |
| Isopropyl palmitate | 2.800 |
| Q2-1401 fluid (87% by weight cyclomethicone, 13% by weight dimethiconol) | 5.600 |
| Bactericide (Triclosan) | 0.070 |
| Fragrance | 0.840 |
| Talc | 1.750 |
| Bentone gel | 2.800 |
| Subtotal concentrate (without propellant) | 35.000 |
| A-31 propellant | 65.000 |
| | 100.000 |

EXAMPLE 13

An aerosol deodorant composition was prepared having the following formulation:

| Ingredients | % by Weight |
|---|---|
| Cyclomethicone | 12.275 |
| Isopropyl palmitate | 1.575 |
| Q2-1401 fluid (87% by weight cyclomethicone, 13% by weight dimethiconol) | 4.000 |
| Bactericide (Triclosan) | 0.050 |
| Finsolv TN | 1.000 |
| Fragrance | 0.950 |
| Talc | 2.100 |
| Zinc Oxide | 1.000 |
| BHT | 0.050 |
| Bentone gel | 2.000 |
| Subtotal concentrate (without propellant) | 25.000 |
| A-46 propellant | 75.000 |
| | 100.000 |

COMPARATIVE EXAMPLE 1

An aerosol deodorant composition was prepared having the following formulation:

| Ingredients | % by Weight |
|---|---|
| Cyclomethicone | 16.275 |
| Isopropyl palmitate | 2.075 |
| Bactericide (Triclosan) | 0.050 |
| Fragrance | 1.500 |
| Talc | 3.100 |
| Bentone gel | 2.000 |
| Subtotal concentrate (without propellant) | 25.000 |
| A-31 propellant | 75.000 |
| | 100.000 |

Tests were conducted to determine the deposition characteristics of the aerosol deodorant compositions of the present invention. The aerosol compositions in containers to be tested were placed in a constant temperature water bath set at 25° C. and left in the water bath for 30 minutes for proper temperature equilibration. A clean watch glass was weighed before the start of the test. The watch glass was then placed in a stand. The 25° C. aerosol can sample is weighed and recorded. Then the 25° C. aerosol can sample is shaken ten times (10×) to ensure full suspension of the active ingredients and then immediately placed six (6) inches away from the center of the watch glass. With the aerosol can held completely vertically and aimed at the center of the watch glass, the product was sprayed for three seconds. The aerosol can was reweighed and the difference in weight was recorded. The watch glass was also reweighed and the difference in weight was recorded.

The following values were calculated:

(1) Weight of product dispensed weight of can before spraying less weight of can after spraying.

(2) Weight of product deposited weight of watch glass after spraying less weight of watch glass before spraying.

(3) % of product actually deposited =

$$\frac{(2) \text{ weight of product deposited}}{(1) \text{ weight of product dispensed}} \times 100.$$

(4) % of product concentrate deposited =

$$\left( \frac{(2) \text{ weight of product deposited}}{(1) \text{ wt. of product dispensed} \times \% \text{ concentrate in product}} \right) \times 100.$$

A comparison was made between Example 8 and Comparative Example 1 using the parameters shown in the following Table 2.

TABLE 2

| Parameter | Comparative Example 1 | Example 8 |
|---|---|---|
| % Concentrate | 25.0 | 25.0 |
| % Propellant | 75.0 | 75.0 |
| Average Initial PSIG | 49 | 50 |
| Average Spray Rate (g/sec) | 0.37 ± 0.02 | 0.41 ± 0.01 |

Table 3 shows the deposition data for Comparative Example 1 as follows:

TABLE 3

| Test # | Weight of Can Before Spraying (g) | Weight of Can After Spraying (g) | (1) Weight of Product Dispensed (g) |
|---|---|---|---|
| 1 | 174.2 | 173.3 | 0.9 |
| 2 | 173.3 | 172.2 | 1.1 |
| 3 | 174.9 | 173.7 | 1.2 |
| 4 | 173.8 | 172.6 | 1.2 |
| 5 | 174.5 | 173.3 | 1.2 |
| 6 | 173.3 | 172.2 | 1.1 |

| Test # | Weight of Watch Glass Before Spraying (g) | Weight of Watch Glass After Spraying (g) | (2) Weight of Product Deposited (g) |
|---|---|---|---|
| 1 | 100.00 | 100.02 | 0.02 |
| 2 | 100.00 | 100.03 | 0.03 |
| 3 | 100.00 | 100.02 | 0.02 |
| 4 | 100.00 | 100.02 | 0.02 |

TABLE 3-continued

| Test # | Weight of Can Before Spraying (g) | Weight of Can After Spraying (g) | Weight of Product Dispensed (g) |
|---|---|---|---|
| 5 | 100.00 | 100.03 | 0.03 |
| 6 | 100.00 | 100.02 | 0.02 |

| Test # | (3) % of Product Actually Deposited | (4) % of Product Concentrate Deposited |
|---|---|---|
| 1 | 2.22 | 8.89 |
| 2 | 2.73 | 10.91 |
| 3 | 1.67 | 6.67 |
| 4 | 1.67 | 6.67 |
| 5 | 2.50 | 10.00 |
| 6 | 1.82 | 7.72 |

Table 4 below shows the deposition data for Example 8:

TABLE 4

| Test # | Weight of Can Before Spraying (g) | Weight of Can After Spraying (g) | (1) Weight of Product Dispensed (g) |
|---|---|---|---|
| 1 | 173.6 | 172.3 | 1.3 |
| 2 | 172.4 | 171.2 | 1.2 |
| 3 | 168.8 | 167.5 | 1.3 |
| 4 | 167.5 | 166.1 | 1.4 |
| 5 | 173.7 | 172.4 | 1.3 |
| 6 | 172.4 | 171.2 | 1.2 |

| Test # | Weight of Watch Glass Before Spraying (g) | Weight of Watch Glass After Spraying (g) | (2) Weight of Product Deposited (g) |
|---|---|---|---|
| 1 | 100.00 | 100.28 | 0.28 |
| 2 | 100.00 | 100.22 | 0.22 |
| 3 | 100.00 | 100.28 | 0.28 |
| 4 | 100.00 | 100.30 | 0.30 |
| 5 | 100.00 | 100.25 | 0.25 |
| 6 | 100.00 | 100.25 | 0.25 |

| Test # | (3) % of Product Actually Deposited | (4) % of Product Concentrate Deposited |
|---|---|---|
| 1 | 21.54 | 86.15 |
| 2 | 18.33 | 73.33 |
| 3 | 21.54 | 86.15 |
| 4 | 21.43 | 82.71 |
| 5 | 19.23 | 76.92 |
| 6 | 20.83 | 83.33 |

The test results are summarized in Table 5 below:

TABLE 5

| Parameter | Comparative Example 1 | Example 8 |
|---|---|---|
| Average Weight of Product Dispensed (3 sec) | 1.10 ± 0.05 | 1.28 ± 0.08 |
| Average Weight of Product Deposited (3 sec) | 0.02 ± 0.01 | 0.26 ± 0.03 |
| Average % Weight of Product Deposited (3 sec) | 2.1 ± 1.8 | 20.5 ± 1.4 |
| Average % Concentrate Deposited (3 sec) | 8.5 ± 1.8 | 81.4 ± 5.2 |
| Average % Concentrate Not Deposited (dispersed into the atmosphere) | 91.5 | 18.6 |

Using the aerosol deodorant composition of the present invention (Example 8), more product was deposited on the target area than the formula without a substantivity fluid (Comparative Example 1). Thus, the aerosol deodorant composition of the present invention provides less of an overspray by depositing 72.9% more concentrate.

What is claimed is:

1. An aerosol deodorant composition comprising:
   an aerosol propellant;
   a volatile low-viscosity fluid;
   an oil absorbent particulate material;
   a silicone polymer; and
   a deodorant active material; wherein said aerosol deodorant composition does not contain an antiperspirant active material.

2. An aerosol deodorant composition according to claim 1, wherein said volatile low-viscosity fluid is a volatile low-viscosity hydrocarbon fluid.

3. An aerosol deodorant composition according to claim 2, wherein said volatile low-viscosity hydrocarbon fluid is a volatile low-viscosity silicone fluid.

4. An aerosol deodorant composition according to claim 3, wherein said volatile low-viscosity silicone fluid is cyclomethicone.

5. An aerosol deodorant composition according to claim 3, wherein said volatile low-viscosity silicone fluid is a straight chain volatile low-viscosity silicone fluid.

6. An aerosol deodorant composition according to claim 5, wherein said straight chain volatile low-viscosity silicone fluid is hexamethyldisiloxane.

7. An aerosol deodorant composition according to claim 5, wherein said straight chain volatile low-viscosity silicone fluid is dimethicone.

8. An aerosol deodorant composition according to claim 1, wherein said oil absorbent particulate material is at least one material selected from the group consisting of talc, starch, clay, microcrystalline cellulose and cereal grain flour.

9. An aerosol deodorant composition according to claim 8, wherein said oil absorbent particulate material is homogeneously dispersed in said volatile low-viscosity fluid.

10. An aerosol deodorant composition according to claim 8, wherein said oil absorbent particulate material has a particle diameter less than 50 microns.

11. An aerosol deodorant composition according to claim 1, wherein said silicone polymer is a silicone gum.

12. An aerosol deodorant composition according to claim 11, wherein said silicone gum is a polydimethylsiloxane gum.

13. An aerosol deodorant composition according to claim 12, wherein said polydimethylsiloxane gum is dimethiconol.

14. An aerosol deodorant composition according to claim 1, further comprising a suspending agent.

15. An aerosol deodorant composition according to claim 14, wherein said clay suspending agent is selected from the group consisting of bentonite gel, hectorite gel, colloidal magnesium aluminum silicate and hydrophobically treated bentonite.

16. An aerosol deodorant composition according to claim 1, wherein said aerosol deodorant composition contains 1% or less alcohol by weight.

17. An aerosol deodorant composition according to claim 16, wherein said aerosol deodorant composition is non-alcoholic.

18. An aerosol deodorant composition according to claim 1, wherein said aerosol deodorant composition is anhydrous.

19. An aerosol deodorant composition according to claim 1, wherein said deodorant active material is at least one material selected from the group consisting of fragrance and bacteriocide.

20. An aerosol deodorant package comprising:

a container;

an aerosol deodorant composition in said container, said aeorsol deodorant composition comprising a propellant; a volatile low-viscosity fluid; an oil absorbent particulate material; a silicone polymer; and a deodorant active material; wherein said aerosol deodorant composition does not contain an antiperspirant active material; and an aerosol delivery system connected to said container, and having a valve, the valve having orifices for passing said aerosol deodorant composition out of the container, the orifices having diameters such that the average delivery rate of the aerosol deodorant composition from the container is at most 0.44 gm/sec.

21. An aerosol deodorant package according to claim 20, wherein said orifices include an orifice in a stem of the valve and a vapor tap orifice, the diameters of the stem orifice and vapor tap orifice being such that the average delivery rate of the aerosol deodorant composition is 0.32-0.44 gm/sec.

22. An aerosol deodorant package according to claim 20, wherein the aerosol delivery system includes a button orifice, the button orifice being in the range of 0.013 inch to 0.020 inch in diameter.

23. An aerosol deodorant package according to claim 20, wherein the aerosol deodorant composition is included in the package at a pressure of 25 to 55 PSIG.

24. A method of applying an aerosol deodorant composition, comprising delivering the aerosol deodorant composition from the aerosol deodorant package according to claim 20 by opening the valve, the aerosol deodorant composition being delivered at an average delivery rate of 0.32-0.44 gm/sec.

25. An aerosol deodorant package comprising:
a container;
an aerosol deodorant composition in said container, wherein said aeorsol deodorant composition consists essentially of a propellant; a volatile low-viscosity fluid; a oil absorbent particulate material; a silicone polymer; and a deodorant active material; and
an aerosol delivery system connected to said container, and having a valve, the valve having orifices for passing said aerosol deodorant composition out of the container, the orifices having diameters such that the average delivery rate of the aerosol deodorant composition from the container is at most 0.44 gm/sec.

26. An aerosol deodorant composition consisting essentially of:
an aerosol propellant;
a volatile low-viscosity fluid;
an oil absorbent particular material;
a silicone polymer; and
a deodorant active material.

27. An aerosol deodorant composition consisting essentially of:
an aerosol propellant;
a volatile low-viscosity fluid;
an oil absorbent particular material;
a silicone polymer;
a deodorant active material; and a suspending agent.

28. An aerosol deodorant composition comprising:
an aerosol propellant;
a volatile low-viscosity fluid;
an oil absorbent particular material;
a silicone polymer; and
a deodorant active material; wherein the silicone polymer is completely dissolved in the volatile low-viscosity fluid.

29. An aerosol deodorant package comprising:
a container;
an aerosol deodorant composition in said container, said aerosol deodorant composition comprising a propellant; a volatile low-viscosity fluid; an oil absorbent particulate material; a silicone polymer; and a deodorant active material; wherein the silicone polymer is completely dissolved in the volatile low-viscosity fluid; and
an aerosol delivery system connected to said container, and having a valve, the valve having orifices for passing said aerosol deodorant composition out of the container, the orifices having diameters such that the average delivery rate of the aerosol deodorant composition from the container is at most 0.44 gm/sec.

* * * * *

UNITED STATES PATENT AND TRADEMARK OFFICE
CERTIFICATE OF CORRECTION

PATENT NO. : 5,082,652
DATED : January 21, 1992
INVENTOR(S) : MAYFIELD et al

It is certified that error appears in the above-identified patent and that said Letters Patent is hereby corrected as shown below:

On the Title Page, left-hand column:   Please add assignee

--[73]  Assignee:  The Mennen Company--.

Signed and Sealed this

Eighteenth Day of May, 1993

Attest:

MICHAEL K. KIRK

Attesting Officer      Acting Commissioner of Patents and Trademarks